United States Patent [19]

Scott et al.

[11] Patent Number: 5,744,658

[45] Date of Patent: *Apr. 28, 1998

[54] CHEMICAL PROCESS

[75] Inventors: John David Scott, Cheshire; Rachel Anne Steven, Manley, both of England

[73] Assignee: Imperial Chemical Industries PLC, London, England

[*] Notice: The term of this patent shall not extend beyond the expiration date of Pat. No. 5,243,107.

[21] Appl. No.: 683,402

[22] Filed: Jul. 18, 1996

Related U.S. Application Data

[63] Continuation of Ser. No. 83,691, Jun. 30, 1993, Pat. No. 5,382,722, and Ser. No. 11,537, Feb. 1, 1993, Pat. No. 5,395,996, said Ser. No. 83,691, is a continuation of Ser. No. 755,554, Sep. 5, 1991, Pat. No. 5,145,826, said Ser. No. 11,537, is a continuation of Ser. No. 804,550, Dec. 11, 1991, Pat. No. 5,243,105, which is a continuation of Ser. No. 676,703, Mar. 29, 1991, abandoned.

[30] Foreign Application Priority Data

Mar. 29, 1996 [GB] United Kingdom ............... 9007029

[51] Int. Cl.$^6$ ................ C07C 17/08; C07C 17/00
[52] U.S. Cl. ............ 570/166; 570/165; 570/167; 570/168; 570/169
[58] Field of Search ............... 570/166, 165, 570/167, 168, 169

[56] References Cited

U.S. PATENT DOCUMENTS

| | | | |
|---|---|---|---|
| 2,005,710 | 6/1935 | Daudt et al. | 570/168 |
| 2,637,747 | 5/1953 | McBee | 570/167 |
| 4,158,675 | 6/1979 | Potter | 570/169 |
| 4,605,798 | 8/1986 | Abel et al. | 570/168 |
| 4,922,037 | 5/1990 | Manzer | 570/168 |
| 5,157,172 | 10/1992 | Wanzke et al. | 570/168 |
| 5,243,105 | 9/1993 | Scott et al. | 570/169 |
| 5,243,107 | 9/1993 | Scott et al. | 570/169 |
| 5,334,786 | 8/1994 | Koyama et al. | 570/168 |
| 5,382,722 | 1/1995 | Scott et al. | 570/169 |
| 5,395,996 | 3/1995 | Scott et al. | 570/169 |
| 5,444,171 | 8/1995 | Ohno et al. | 570/169 |

*Primary Examiner*—Alan Siegel
*Attorney, Agent, or Firm*—Pillsbury Madison & Sutro LLP

[57] ABSTRACT

A method of producing 1,1,1,2-tetrafluoroethane in two separation reaction zones involving (1) reaction of trichloroethylene and hydrogen fluoride to produce 1,1,1-trifluoro-2-chloroethane and (2) reaction of the 1,1,1-trifluoro-2-chloroethane and hydrogen fluoride to produce 1,1,1,2-tetrafluoroethane wherein both reactions are carried out at superatmospheric pressure, reaction (2) is carried out at a temperature in the range of 250°–450° C., reaction (1) is carried out at a temperature in the range of 200°–400° C. but below that used in reaction (2) and unconverted 1,1,1-trifluoro-2-chloroethane is recycled for further reaction with hydrogen fluoride.

2 Claims, No Drawings

CHEMICAL PROCESS

This is a continuation of Ser. No. 08/083,691, filed Jun. 30, 1993 now U.S. Pat. No. 5,382,722, and of Ser. No. 08/011,537, filed Feb. 1, 1993 now U.S. Pat. No. 5,395,996, said Ser. No. 08/083,691 being a continuation of Ser. No. 07/755,554, filed Sep. 5, 1991, now U.S. Pat. No. 5,145,826, and said Ser. No. 08/011,537 being a continuation of Ser. No. 07/804,550, filed Dec. 11, 1991, now U.S. Pat. No. 5,243,105, which is a continuation of Ser. No. 07/676,703, filed Mar. 29, 1991, now abandoned.

This invention relates to a chemical process and more particularly to a process for the manufacture of 1,1,1,2-tetrafluoroethane, known generally as HFA 134a.

RELATED APPLICATIONS

This is a continuation-in-part of Ser. No. 08/83,691, filed Jun. 30, 1993, and of Ser. No. 08/11,537, filed Feb. 1, 1993. Said Ser. No. 08/83,691 is a continuation of Ser. No. 07/755,554, filed Sep. 5, 1991, now U.S. Pat. No. 5,243,107 and said Ser. No. 08/011,537 is a continuation of Ser. No. 07/804,550, filed Dec. 11, 1991, now U.S. Pat. No. 5,243,105, which is a continuation of Ser. No. 07/676,703, filed Mar. 29, 1991, now abandoned. The contents of these earlier U.S. applications including the disclosure of British application No. 9007029.3, filed Mar. 29, 1990 on which the U.S. applications are based are incorporated herein, by reference.

Several methods have been proposed for the manufacture of 1,1,1,2-tetrafluoroethane (HFA 134a) which is a useful replacement for CFCs in refrigeration and other applications. In United Kingdom Patent Specification No. 1,589, 924, there is described the production of HFA 134a by the vapour phase fluorination of 1,1,1-trifluoro-2-chloroethane (HCFC 133a) which is itself obtainable by the fluorination of trichloroethylene as described in United Kingdom Patent Specification No. 1,307,224. Unfortunately, the yield of HFA 134a obtained in practice is significantly less than the calculated equilibrium yield. The formation of HFA 134a as a minor product of the fluorination of trichloroethylene is described in United Kingdom Patent Specification No. 819, 849, the major reaction product being HCFC 133a.

In WO 90/08755 there is described the conversion of trichloroethylene to HFA 134a wherein the two-stage reactions are carried out in a single reaction zone with recycle of part of the product stream.

Carrying out the conversion in a single reaction zone as described in WO 90/08755 suffers from the serious drawback that the fluorination catalyst tends to deactivate rapidly, largely as a result of carbon deposition, and thus has a very short lifetime. For example, we have found that operation of the single zone process using a chromia catalyst at 340° C. with a feed containing 10 molar % trichloroethylene and a contact time of 20 seconds resulted in fall in conversion of organics in the feed stream to HFA 134a to below 10% in a matter of less than 24 hours and that in order to maintain a conversion of 10% it was necessary to raise the temperature of the catalyst by some 30° to 40° C. (from 340° to 370°–380°) over a period of 4 days. This problem of short catalyst lifetime renders the single stage process unsuitable of practical adoption.

It has now been found that a two-step reaction sequence carried out in separate reaction zones as hereinafter described provide significantly improved yields of the desired product with high catalyst selectivity and high catalyst productivity and with an increased catalyst lifetime.

Broadly speaking, the process of the invention provides for the production of 1,1,1,2-tetrafluoroethane in two separation reaction zones involving (1) the reaction of trichloroethylene and hydrogen fluoride to produce 1,1,1-trifluoro-2-chloroethane and (2) reaction of the 1,1,1-trifluoro-2-chloroethane and hydrogen fluoride to produce 1,1,1,2-tetrafluoroethane wherein both reaction are carried out at superatmospheric pressure, reaction (2) is carried out at a temperature in the range of 250°–450° C., reaction (1) is carried out at a temperature in the range of 200°–400° C. but below that used in reaction (2) and unconverted 1,1,1-trifluoro-2-chloroethane is recycled for further reaction with hydrogen fluoride.

One embodiment for the manufacture of 1,1,1,2-tetrafluoroethane according to the invention comprises the steps of:

(A) contacting a mixture of 1,1,1-trifluoro-2-chloroethane and hydrogen fluoride with a fluorination catalyst at a temperature in the range of about 280° to 450° C. in a first reaction zone to form a product containing 1,1,1,2-tetrafluoroethane and hydrogen chloride together with unreacted starting material, (B) passing the product of step A together with trichloroethylene to a second reaction zone containing a fluorination catalyst at a temperature in the range of about 200°–400° C. but lower than the temperature in step A to form a product containing 1,1,1-trifluoro-2-chloroethane, 1,1,1,2-tetrafluoroethane, hydrogen chloride and trichloroethylene, (C) treating the product of step B to separate 1,1,1,2-tetrafluoroethane and hydrogen chloride from 1,1,1-trifluoro-2-chloroethane, unreacted hydrogen fluoride and trichloroethylene, (D) feeding the 1,1,1-trifluoro-2-chloroethane mixture obtained from step (C) together with hydrogen fluoride to said first reaction zone (step A), and (E) recovering 1,1,1,2-tetrafluoroethane from the 1,1,1,2-tetrafluoroethane and hydrogen chloride separated out in step (C).

For ease of reference, the method represented by steps (A)–(E) above is referred to herein as Embodiment I. In an alternative embodiment (Embodiment II), the method for the manufacture of 1,1,1,2-tetrafluoroethane comprises the steps of:

(A) contacting a mixture of trichloroethylene and hydrogen fluoride with a fluorination catalyst under super atmospheric pressure at a temperature in the range of about 200° to 400° C. in a first reaction zone to form a product containing 1,1,1-trifluoro-2-chloroethane and hydrogen chloride together with unreacted starting materials, (B) passing the product of step A together with hydrogen fluoride to a second reaction zone containing a fluorination catalyst at a temperature in the range of about 280°–450° C. but higher than the temperature in step A to form a product containing 1,1,1,2-tetrafluoroethane, 1,1,1-trifluoro-2-chloroethane and hydrogen chloride, (C) treating the product of step B to separate 1,1,1,2-tetrafluoroethane and hydrogen chloride from 1,1,1-trifluoro-2-chloroethane and unreacted hydrogen fluoride, (D) feeding the 1,1,1-trifluoro-2-chloro-ethane mixture obtained from step C together with trichloroethylene and hydrogen fluoride to said first reaction zone (step A), and (E) recovering 1,1,1,2-tetrafluoroethane from the 1,1,1,2-tetrafluoroethane and hydrogen chloride separated out in step C.

It is to be appreciated that in Embodiment I steps (A) and (B) are the reverse of steps A and B of Embodiment II. However, in both embodiments, steps A and B are carried out at superatmospheric pressure, the hydrogen fluoride-1,1,1-trifluoro-2-chloroethane reaction is carried out at 280°–450° C., the trifluoroethylene and hydrogen fluoride are reacted at 200°–400° C. but at a temperature lower than the hydrogen fluoride-1,1,1-trifluoro-2-chloroethane reactions and non-converted 1,1,1-trifluoro-2-chloroethane is recycled for reaction with hydrogen fluoride.

The fluorination catalyst employed in steps A and B of the two embodiments of the invention may be the same or different and may be supported or unsupported. Any of the fluorination catalysts described in the prior art may be used including various inorganic compounds, for example, oxides, halides and oxyhalides of metals such as aluminum, cobalt, manganese, iron and especially chromium. Suitable chromium-containing catalysts include the oxide, hydroxide, oxyhalide, halides, inorganic acid salts, basic chromium fluoride and the catalysts described in United Kingdom Patent Specification No. 1,307,224. Preferred catalysts are chromia and a zinc or nickel promoted chromia. Such catalysts may be given a perfluorination treatment by passing hydrogen fluoride with or without nitrogen diluent over the catalyst at about 250°–450° C. to condition the catalyst prior to use.

The catalysts may be compressed into pellets and used in a fixed bed or, alternatively, catalysts of appropriate particle size may be used in a moving bed such as a fluidized bed.

A wide range of amounts of hydrogen fluoride may be employed in steps A and B of the method of the invention, ranging from well below the stoichiometric amount to well above this amount Typical amounts include from 1 to 10 moles, and preferably from 2 to 6 moles, of hydrogen fluoride per mole of 1,1,1-trifluoro-2-chloroethane. The product of the reaction step where hydrogen fluoride is reacted with 1,1,1-trifluoro-2-chloroethane (step A in Embodiment I and step B in Embodiment II) will usually contain unreacted hydrogen fluoride in addition to 1,1,1,2-tetrafluoroethane, hydrogen chloride and by-products. Preferred reaction temperature for this stage of the process are in the range from 285° to 385° C., especially 300° to 385° C., with contact times of from 1 to 100 and preferably from 5 to 30 seconds at a pressure of 5 to 20 bars.

From 10 to 100, preferably from 15 to 60, moles of hydrogen fluoride per mole of trichloroethylene are typically employed for this reaction step in either embodiment. Again, the reaction product of this step will normally contain unreacted hydrogen fluoride and perhaps low levels of unreacted trichloroethylene. Contact times of up to 100 seconds, preferably 5 to 30 seconds may be used, typically at 220°–350° C. and 5 to 20 bars pressure.

Steps A and B of the method and usually at least step C of both embodiments will usually be carried out under the same superatmospheric pressure which may be, for example, 1 to 30 bars. Preferably, the pressure for steps A, B and C is at least 2 bars and more preferably at least 5 bars.

In general, increasing the pressure results in an increase in catalyst productivity. Usually, the pressure will not exceed 30 bars although pressure beyond this may be used if desired. The operating pressure is usually dependent on the product work-up scheme employed but as noted, is generally within the range of from 1 to 30 bars.

The reaction and separation steps which make up the method of the invention may be performed using conventional equipment and techniques. Thus, for example, recovery of 1,1,1,2-tetrafluoroethane in step E may be effected by washing the gaseous tetrafluoroethane with water and aqueous sodium hydroxide solution and then drying and condensing the tetrafluoroethane.

It is preferred that the method of the invention is operated continuously. In practice, however, catalyst deactivation usually occurs requiring discontinuous operation of the process to permit catalyst regeneration or reactivation which may be conveniently effected by passing air or a mixture of air and inert gas, for example nitrogen, over the catalyst at a temperature in the range of 300° to 500° C. A preferred catalyst reactivation process comprises heating the catalyst in a mixture of air and hydrogen fluoride, the resulting hot hydrogen fluoride being useable directly in the method according to the invention. The frequency of catalyst regeneration may be reduced if air is added to the reaction mixture in steps A and B.

A particularly useful feature of the invention is that the exothermic conversion of trichloroethylene to 1,1,1-trifluoro-2-chloroethane may be performed in a low cost adiabatic reactor, thereby providing significant cost advantages over reactor systems employing internal cooling surfaces. If desired, the reaction between the 1,1,1-trifluoro-2-chloroethane and trichloroethylene may be carried out in an adiabatic reactor. An interstage heater may be used to raise the temperature between the two reactions in the case of Embodiment II.

As stated hereinabove, the temperature employed in step (1) of the process where the trichloroethylene is reacted with hydrogen fluoride (e.g. step B in Embodiment I) is lower than the temperature employed in step (2) where the 1,1,1-trifluoro-2-chloroethane is reacted with hydrogen fluoride. As a consequence, the reaction stream from step (A) to step (B) in Embodiment I may require cooling to or to below the temperature used in the reaction where trichloroethylene is reacted with hydrogen fluoride (e.g. step B of Embodiment I) and a useful technique comprises mixing the trichloroethylene feed with the reaction stream in advance of the trichloroethylene reactor; in this way the reaction stream is cooled by the trichloroethylene whilst at the same time the trichloroethylene is heated, thereby reducing the need for external heating.

As stated, the 1,1,1,2-tetrafluoroethane production process is carried out in two reaction zones operated at different temperatures. The two reaction zones may be provided in separated reactors if desired, but alternatively, the process may be carried out in a single reactor containing both of the reaction zones. Thus, for example, the reactor may comprise a series of tubes through which the reactant streams are fed, each tube containing the fluorination catalyst and having a lower temperature length and a higher temperature length for the reactions indicated. Trichloroethylene and hydrogen fluoride, together with a prior reaction stream may be fed into the lower temperature end of the tube and a product stream containing 1,1,1,2-tetrafluoroethane is withdrawn from the higher temperature end of the tube. As noted, the reaction vessel may be an adiabatic reactor.

Separation of 1,1,1,2-tetrafluoroethane and hydrogen chloride from the product stream of the process may be effected by a distillation technique. The separation of hydrogen chloride from the product stream is desirable since the presence of hydrogen chloride would reduce the degree of conversion of 1,1,1-trichloro-2-chloroethane to 1,1,1,2-tetrafluoroethane; for this reason it is preferred to remove the hydrogen chloride as completely as is reasonably practicable.

Embodiment I of the invention is advantageous in that the HFA 134a collected from step B of this embodiment may contain only a small amount, for example 10 to 40 ppm, of the toxic impurity 1-chloro-2,2-difluoroethylene, commonly known as 1122 compared with the amount, for example 200 to 1000 ppm, contained in HFA 134a produced in step A of this process or in the Embodiment II process. In either embodiment, however, the procedure employed in the work-up of the product stream from step B (including the separation step C) will usually contain one or more provisions for removing the 1122 which owing to its similar boiling point to HFA 134a tends to stay with the HFA 134a during the work-up operations.

At least part of the 1122 can be removed from the product stream prior to separation step C by contacting the product stream from step B together with hydrogen fluoride (already present in the product stream) over a fluorination catalyst such as chromia at a temperature in the range of 150° to 250° C. Any 1122 present in the HFA 134a after step C can be removed by azeotropic distillation or extractive distillation and/or by contacting the HFA 134a with a zeolite molecular sieve.

The invention is illustrated but not limited by the following Example.

EXAMPLE 1

To demonstrate Embodiment II of the invention, 1,1,1,2-tetrafluoroethane was produced in a two-reactor system comprising a first reactor for converting trichlorethylene to 1,1,1-trifluoro-2-chloroethane and a second reactor for converting the 1,1,1-trifluoro-2-chloroethane to 1,1,1,2-tetrafluoroethane (i.e. according to Embodiment II of the invention). The trichloroethylene and hydrogen fluoride were fed to the first, low temperature reactor (273° C.) at 13.5 bar. g. to convert the trichloroethylene selectively to 1,1,1-trifluoro-2-chloroethane (133a). The products of the first reactor were then passed to a second, higher temperature, reactor operating at 366° C. and 13.5 bar. g where the 133a produced in stage 1 was partially converted to HFA 134a. 133a was included in the feed to the 1st reactor together with the hydrogen fluoride and trichloroethylene to simulate a typical feed including recycle of 133a, HF and a small amount of trichloroethylene from the second reactor. Using an HF:Organics molar ratio of 3.5:1 at the first stage, and a 15% molar trichlorethylene content in the organics feed 133a to give a contact time of 13.5 seconds in each reactor, the reaction efficiencies for the two reactor system were measured and these are presented in Table 1.

For purposes of comparison, the above procedure was repeated using the same reactors but carrying out the reactions in both reactors at atmospheric pressure (contact time approximately 1 second). Reaction efficiencies are shown in Table 1. The results in Table 1 show the much improved catalyst productivity achieved by carrying out the reaction in both reactors at superatmospheric pressure.

The process according to the invention (Embodiment II) was found to give significant catalyst productivity advantages as well as high reaction selectivity.

EXAMPLE 2

To demonstrate Embodiment I of the invention, the above order of the series reactors were reversed. In this scheme, the same trichlorethylene and HF feed rates were employed with the same 133a and HF additions to simulate a recycle feed (as above), recycle rates, but the trichloroethylene was introduced into the reactor scheme between the two reactors. The reactor temperatures were also reversed so that the first reactor was operated at the higher reaction temperature (366° C.) for HFA 134a production. Results are also shown in Table 1.

As will be seen, Embodiment I was found to give significant reaction conversion advantages to HFA 134a as well as an increase in reaction selectivity. In addition, Embodiment I also has the advantage of significantly decreasing the level of the toxic unsaturated impurity 1-chloro-2,2-difluoroethylene in the 134a product from 933 ppm in the Embodiment II process to 16 ppm in the Embodiment I process.

TABLE 1

| Reactor No. 1 | Reactor No. 2 | Trichloro-ethylene Conversion (%) | % Yields from trichloroethylene R133a R134a By-Products | | R134a Selectivity (%) | R134a + R133a Selectivity (%) | $CHCl{:}CF_2$ Level in organic product (ppm) |
|---|---|---|---|---|---|---|---|
| Comparison (atmospheric pressure) 273° C. (after 24 hrs.) | 366° C. | 97.0 | 59.8 11.0 | 26.2 | 27.01 | 88.7 | |
| Embodiment II Series Reactors, superatmospheric pressure 273° C. | 366° C. | 99.5 | 16.7 6.5 | 76.3 | 76.6 | 91.4 | 933 |
| Embodiment I (Reverse Series Reactors) 366° C. | 275° | 97.8 | 0.0 4.1 | 93.7 | 95.8 | 95.8 | 16 |

EXAMPLE 2

For purposes of comparison a reactor was charged with chromia catalyst and used to react trichloroethylene with hydrogen fluoride at 250° C. and atmospheric pressure with a contact time of 10 seconds. The conversion and selectivities observed are shown in Table 2.

For further purposes of comparison a second reactor was charged with chromia catalyst and the product stream from the first reactor (above) was passed through the second reactor at a temperature of 360° C. and atmospheric pressure with a contact time of 1 second. Using an HF:Organics molar ratio of 3:5:1 and a 15% molar trichloroethylene content in the organics feed, reaction efficiencies were measured and conversion and selectivities are shown in Table 2.

To demonstrate the invention, the positions of the two reactors were reversed and the trichloroethylene was fed to the product stream between the reactors. The conversions and selectivities are shown in Table 2.

TABLE 2

| Reactor No. 1 | Reactor No. 2 | Trichloro-ethylene Conversion (%) | % Yields from trichloroethylene R133a R134a By-Products | | R134a Selectivity (%) | R134a + R133a Selectivity (%) | CHCl:CF$_2$ Level in organic product (ppm) |
|---|---|---|---|---|---|---|---|
| Comparison (One reactor only) 250° C. Embodiment II | — | 97.6 | 90.5 6.7 | 0.4 | 0.4 | 93.2 | 31 |
| (Series) Reactors, 250° C. Embodiment I | 360° C. | 96.2 | 41.9 11.9 | 42.4 | 44.1 | 87.6 | 979 |
| (Reverse Series Reactors) 360° C. | 250° C. | 98.2 | 2.5 8.2 | 87.5 | 89.1 | 91.7 | 29 |

What is claimed is:

1. A method for the manufacture of 1,1,1,2-tetrafluoroethane which comprises the steps of:
    (a) contacting a mixture of 1,1,1-trifluoro-2-chloroethane and hydrogen fluoride with a fluorination catalyst at superatmospheric pressure and a temperature in the range of about 280° to 450° C. in a first reaction zone to form a product containing 1,1,1,2-tetrafluoroethane and hydrogen chloride together with unreacted starting materials;
    (b) passing the total product of step (a) together with trichloroethylene to a second reaction zone containing a fluorination catalyst at superatmospheric pressure and a temperature in the range of about 200°–400° C. but lower than the temperature in step (a) to form a product containing 1,1,1,2-tetrafluoroethane and 1,1,1-trifluoro-2-chloroethane;
    (c) treating the product of step (b) to separate 1,1,1,2-tetrafluoroethane from 1,1,1-trifluoro-2-chloroethane;
    (d) feeding the 1,1,1-trifluoro-2-chloroethane from step (c) together with hydrogen fluoride to said first reaction zone (step(a)); and
    (e) collecting the 1,1,1,2-tetrafluoroethane separated out in step (c).

2. A method for the manufacture of 1,1,1,2-tetrafluoroethane which comprises the steps of:
    (a) contacting a mixture of 1,1,1-trifluoro-2-chloroethane and hydrogen fluoride with a fluorination catalyst at superatmospheric pressure and a temperature in the range of about 280° to 450° C. in a first reaction zone to form a product containing 1,1,1,2-tetrafluoroethane and hydrogen chloride together with unreacted starting materials;
    (b) passing the product of step (a) together with trichloroethylene to a second reaction zone containing a fluorination catalyst at a temperature in the range of about 200°–400° C. but lower than the temperature in step (a) to form a product containing 1,1,1,2-tetrafluoroethane and 1,1,1-trifluoro-2-chloroethane;
    (c) treating the product of step (b) to separate 1,1,1,2-tetrafluoroethane from 1,1,1-trifluoro-2-chloroethane;
    (d) feeding the 1,1,1-trifluoro-2-chloroethane from step (c) together with hydrogen fluoride to said first reaction zone (step(a)); and
    (e) collecting the 1,1,1,2-tetrafluoroethane separated out in step (c).

* * * * *